United States Patent [19]
Lochead et al.

[11] Patent Number: 4,914,092
[45] Date of Patent: Apr. 3, 1990

[54] BENZOTHIAZEPIN-4-ONE DERIVATIVES, THEIR PREPARATION AND THEIR APPLICATION IN THERAPY

[75] Inventors: Alistair Lochead, Paris; Jean C. Muller, Morsang Sur Orge; Colombe Denys, Bourg La Reine; André Dumas, Palaiseau, all of France

[73] Assignee: Synthelabo, Paris, France

[21] Appl. No.: 339,978

[22] Filed: Apr. 18, 1989

[30] Foreign Application Priority Data

Apr. 19, 1988 [FR] France .................. 88 05131

[51] Int. Cl.$^4$ ........... A61K 31/55; C07D 281/10
[52] U.S. Cl. ............................... 514/211; 540/491
[58] Field of Search ..................... 514/211; 540/491

[56] References Cited

U.S. PATENT DOCUMENTS

| | | | |
|---|---|---|---|
| 3,757,008 | 9/1973 | Hellerbach et al. | 260/239.3 D |
| 4,729,994 | 3/1988 | Carson | 514/211 |
| 4,743,599 | 5/1988 | Muller et al. | 540/491 |

Primary Examiner—Robert T. Bond
Attorney, Agent, or Firm—Fleit, Jacobson, Cohn, Price, Holman & Stern

[57] ABSTRACT

A compound, in the form of a pure diastereoisomer or mixture thereof, which is a benzothiazepin-4-one derivative of formula (I):

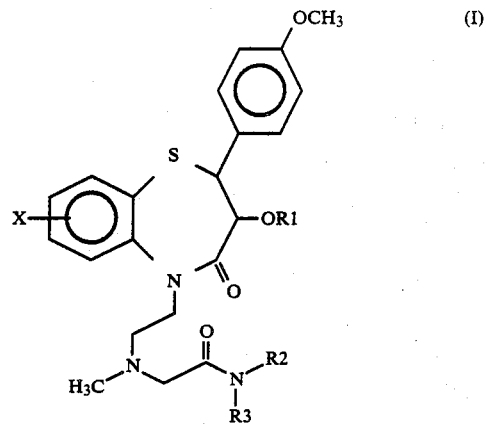

in which:
R1 is hydrogen or a $C_2$–$C_4$ alkanoyl group;
R2 and R3 independently each is hydrogen, a linear or branched $C_1$–$C_4$ alkyl group, a $C_3$–$C_5$ cycloalkyl group, a phenyl group, a benzyl group or a phenethyl group, or R2 and R3 together form, with the nitrogen atom to which they are attached, a pyrrolidinyl, 2,2-dimethylpyrrolidinyl, piperidyl, 4-phenylpiperidyl, 4-(3-methoxyphenyl)piperidyl, 4-(4-fluorobenzoyl)-piperidyl, 1,2,3,6-tetrahydropyridyl, perhydroazepinyl, perhydroazocinyl, 1,3-thiazolidinyl, thiomorpholinyl, morpholinyl, 2,3-dihydroindolyl, 1,2,3,4-tetrahydroisoquinolyl, 6-methoxy-1,2,3,4-tetrahydroisoquinolyl, 6,7-dimethoxy-1,2,3,4-tetrahydroisoquinolyl or 2,3,4,5-tetrahydro-1H-benz[b]azepinyl group; and
X is hydrogen or chlorine;
or a pharmacologically acceptable acid addition salt thereof.

12 Claims, No Drawings

BENZOTHIAZEPIN-4-ONE DERIVATIVES, THEIR PREPARATION AND THEIR APPLICATION IN THERAPY

The present invention relates to 5-{2-[N-(2-amino-2-oxoethyl) methylamino]ethyl}-3-hydroxy-2-(4-methoxyphenyl)-2,3-dihydro-1,5 (5H)-benzothiazepin-4-one derivatives, to their preparation, to compositions containing them and to their application in therapy.

The present invention provides a compound, in the form of a pure diastereoisomer or a mixture thereof, which is a benzothiazepin-4-one of formula (I) depicted in the Scheme below in which:

R1 is hydrogen or a $C_2$–$C_4$ alkanoyl, for example $COCH_3$, group R2 and R3 independently each is hydrogen, a linear or branched $C_1$–$C_4$ alkyl, for example methyl, ethyl, $iC_3H_7$, $iC_4H_9$ or $t$–$C_4H_9$ group, a $C_3$–$C_5$ cycloalkyl, for example cyclopropyl, group, a phenyl group, a benzyl group or a phenethyl group, or R2 and R3 together form, with the nitrogen atom to which they are attached, a pyrrolidinyl, 2,2-dimethylpyrrolidinyl, piperidyl, 4-phenylpiperidyl, 4-(3-methoxyphenyl)piperidyl, 4-(4-fluorobenzoyl)piperidyl, 1,2,3,6-tetrahydropyridyl, perhydroazepinyl, perhydroazocinyl, 1,3-thiazolidinyl, thiomorpholinyl, morpholinyl, 2,3-dihydroindolyl, 1,2,3,4-tetrahydroisoquinolyl, 6-methoxy-1,2,3,4tetrahydroisoquinolyl, 6,7-dimethoxy-1,2,3,4tetrahydroisoquinolyl or 2,3,4,5-tetrahydro-1H-benz(b)-azepinyl group; and X is hydrogen or chlorine; or a pharmacologically acceptable acid addition salt thereof.

Preferred compounds in which R2 and R3 are separate substituents are those in which R3 is a benzyl group, especially 3-acetyloxy-2-(4-methoxyphenyl)-5-{2-[N-{2-oxo-2[N-(phenylmethyl)methylamino]ethyl} methylamino]ethyl]-2,3-dihydro-1,5(5H)-benzothiazepin-4-one.

Preferred compounds in which R2 and R3 are joined are those in which R2 and R3 together form, with the nitrogen atom to which they are attached, a 4-phenylpiperidyl group (especially 3-acetyloxy-2-(4-methoxyphenyl)-5-[2-{N-[2-oxo-2-(4-phenyl-1-piperidyl)ethyl]-methylamino}ethyl]-2,3-dihydro-1,5(5H)-benzothiazepin-4-one), a perhydroazepinyl group (especially 3-acetyloxy-2-(4-methoxyphenyl)-5-[2-{N-[2-oxo-2-(perhydro-1-azepinyl)ethyl]methylamino}ethyl]-2,3-dihydro-1,5(5H)-benzothiazepin-4-one, 9-chloro-3-hydroxy-2-(4-methoxyphenyl)-5-[2-{N-[2-oxo-2-(perhydro-1-azepinyl) ethyl]methylamino}ethyl]-2,3-dihydro-1,5(5H)-benzothiazepin-4-one, or 3-acetyloxy-9-chloro-2-(4-methoxyphenyl)-5-[2-{N-[2-oxo-2-(perhydro-1-azepinyl)ethyl]methylamino}ethyl]-2,3-dihydro-1,5(5H)-benzothiazepin-4-one), or an unsubstituted or substituted 1,2,3,4-tetrahydroisoquinolyl group (especially 3-acetyloxy-2-(4-methoxyphenyl)-5-[2-{N-{2-(1,2,3,4-tetrahydro-2-isoquinolyl)-2-oxoethyl]methylamino}ethyl]-2,3-dihydro-1, 5(5H)-benzothiazepin-4one, 3-acetyloxy-2-(4-methoxphenyl)-5-[2-{N-[2-(6-methoxy-1,2,3,4-tetrahydro-2-isoquinolyl)-2-oxoethyl]methylamino}ethyl]-2,3-dihydro-1,5(5H)-benzothiazepin-4-one, 9-chloro-3-hydroxy-2-(4-methyoxyphenyl)-5-[2-{N-[2-(6-methoxy-1,2,3,4-tetrahydro-2-isoquinolyl)-2-oxoethyl]-methylamino}-ethyl]-2,3-dihydro-1,5(5H)-benzothiazepin-4-one or 3-acetyloxy-9-chloro-2-(4-methoxyphenyl)-5-[2-N-[2-(1,2,3,4-tetrahydro-2-isoquinolyl)-2-oxoethyl]methylamino}ethyl]-2,3-dihydro-1,5(5H)-benzothiazepin-4-one.

SCHEME

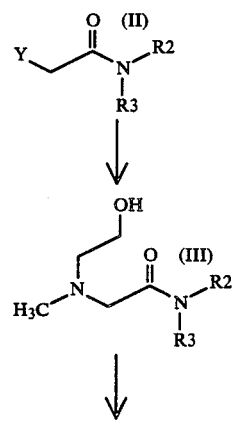

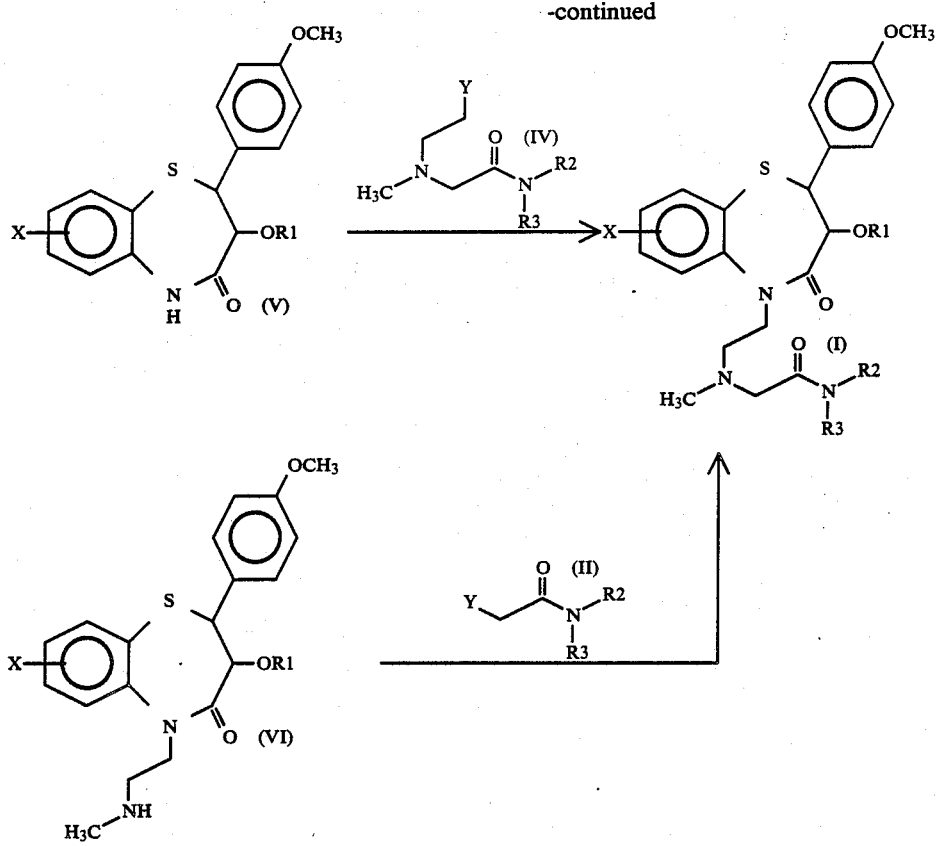

Since the carbon atoms at the 2- and 3- positions are asymmetric, the compounds can exist in various diastereoisomeric, racemic or optically pure forms, the preferred form being the (+)-cis-(2S,3S) form. These various forms form part of the invention.

Examples of salts include hydrochloride, oxalate, dioxalate and maleate salts.

According to the invention, the compounds of formula (I) or pharmacologically acceptable acid addition salts thereof may be prepared according to the scheme given above.

The present invention also provides a process for producing a compound of formula (I) or a pharmacologically acceptable acid addition salt thereof wherein a benzothiazepinone of formula (V) in which R1 and X are as defined above is reacted with a halogenated amine of formula (IV), in which R2 and R3 are as defined above and Y is a halogen, such as chlorine or bromine, and the compound of formula (I) thus obtained is, if desired, converted to a pharmalogically acceptable acid addition salt thereof.

The present invention additionally provides a process for producing a compound of formula (I) or a pharmacologically acceptable acid addition salt thereof wherein a benzothiazepinone of formula (VI), in which R1 and X are as defined above, is reacted with a halogenated derivative of formula (II), in which R2 and R3 are as defined above and Y is a halogen, such as chlorine or bromine, and the compound of formula (I) thus obtained is, if desired, converted to a pharmacologically acceptable acid addition salt thereof.

These two reactions, between an amine and a halogenated derivative, are traditional, and hence proceed under conditions well known to those versed in the art, that is to say, for example, in an aprotic solvent such as acetone or 2-butanone, at reflux temperature, in the presence of a base capable of binding to the acid liberated, for example potassium carbonate, and optionally in the presence of a phase transfer catalyst such as tetra-n-butylammonium iodide. It is self-evident that it is possible to convert a compound of formula (I) in which R1 denotes hydrogen to a compound of formula (I) in which R1 is an alkanoyl group by acylation, and that the reverse conversion is possible by hydrolysis.

The benzothiazepinones of formula (V) are described in U.S. Pat. No. 3,562,257; those of formula (VI) are described in EP-A No. 158,339 and EP-A No. 158,340.

The halogenated amine of formula (IV) may be prepared, for example, by reacting an alcohol of formula (III) in which R2 and R3 are as defined above, with a halogenating agent such as thionyl chloride. The amino alcohol of formula (III) can itself be prepared according to any known method, for example from a halogenated derivative of formula (II) in which R2, R3 and Y are as defined above and 2-(methylamino)ethanol.

The compounds of formula (II , described in the literature, are obtainable from chloroacetyl chloride and an amine of formula HNR2R3 in which R2 and R3 are as defined above.

The Examples which follow further illustrate the preparation of a few compounds according to the invention. Elemental microanalyses and IR and NMR spectra confirm the structures of the products obtained.

The numbers shown in brackets for each Example correspond to those in the table given later.

EXAMPLE 1 (COMPOUND NO. 17)

(+)-cis-(2S,3S)-3-Acetyloxy-2-(4-methoxyphenyl)-5-[2-{N[2-oxo-2-(4-phenyl-1-piperidyl)ethyl methylamino}ethyl]2,3-dihydro-1,5(5H)-benzothiazepin-4-one oxalate A mixture of 3 g (6.9 mmol) of (+)-cis-(2S,3S)-3-3-acetyloxy-2-(4-methyoxyphenyl)-5-[2-(methylamino)ethyl]-2,3-dihydro-1,5(5H)-benzothiazepin-4-one in hydrochloride form, 1.96 g (8.2 mmol) of 1-(2-chloroacetyl)-4-phenyl-piperidine and 4 g (29 mmol) of potassium carbonate in 80 ml of 2-butanone is heated under reflux for 8 h.

The mixture is filtered, the filtrate is evaporated and the residue is purified by chromatography on silica gel.

The oil obtained is taken up with ethanol and treated with oxalic acid, and the precipitate is filtered off and recrystallized in ethanol. 2.2 g of oxalate are isolated.

Melting point: 167° $[\alpha]_D^{20} = +69.1°$ (c=0.5; MeOH).

EXAMPLE 2 (COMPOUND NO. 28)

(+)-cis-(2S,3S)-3-Acetyloxy-2-(4-methoxyphenyl)-5-[2-{N[2(1,2,3,4-tetrahydro-2-isoquinolyl)-2-oxoethyl]methylamino}ethyl]-2,3-dihdyro-1,5(5H)-benzothiazepin-4-one oxalate A mixture of 10 g (23 mmol) of (+)-cis-(2S,3S)-3-acetyloxy-2-(4-methoxyphenyl)5-[2-(methylamino)ethyl]-2,3-dihydro-1,5(5H)-benzothiazepin-4-one in hydrochloride form, 5.28 g (25 mmol) of 2-(2-chloroacetyl)-1,2,3,4tetrahydroisoquinoline and 13 g of potassium carbonate in 200 ml of 2-butanone is heated under reflux for 10 hours.

The mixture is filtered, the filtrate is evaporated and the residue is taken up with 80 ml of chloroform and washed with 50 ml of water. The organic phase is dried over magnesium sulphate and evaporated, and the residual oil is purified by chromatography on silica gel.

10.1 g of free base are obtained, and this is taken up in ethanol and treated with oxalic acid. The precipitate is filtered off and recrystallized in ethanol.

8.03 g of oxalate are isolated.

Melting point: 144° C. $[\alpha]_D° = +77.5°$ C. =0.5; MeOH).

EXAMPLE 3 (COMPOUND NO. 29)

(+)-cis-(2S,3S)-3-Acetyloxy-2-(4-methoxyphenyl)-5-[2-(N[2-(6-methoxy-1,2,3,4-tetrahydro-2-isoquinolyl)-2-oxoethyl]methylamino}ethyl]-2,3-dihydro-1,5(5H)-benzothiazepin-4-one oxalate.

A mixture of 3.77 g (8.6 mmol) of (+)-cis-(2S,3S)-3-acetyloxy-2-(4-methoxyphenyl)-5-[2-(methylamino)ethyl]-2,3-dihydro-1,5(5H)-benzothiazepin-4-one in hydrochloride form, 2.13 g (9.5 mmol) of 2-(2-chloroacetyl)-6-methoxy-1,2,3,4-tetrahydroisoquinoline and 5.2 g (38 mmol) of potassium carbonate in 100 ml of 2-butanone is heated under reflux for 20 h.

The mixture is filtered, the filtrate is evaporated and the residue is taken up with 80 ml of chloroform and washed with 50 ml of water. The organic phase is dried over magnesium sulphate and evaporated, and the residual oil is purified by chromatography on silica gel.

4.19 g of free base are obtained, and this is taken up in ethanol and treated with oxalic acid. The precipitate is filtered off and recrystallized in ethanol.

1.93 g of oxalate are isolated.

Melting point: 142° C. $[\alpha]_D^{20} = +73.3°$ C. =0.5; MeOH).

EXAMPLE 4 (COMPOUND NO. 21)

(+)-cis-(2S,3S)-3-Acetyloxy-2-(4-methoxyphenyl)-5-[2-{N[2-oxo-2-(perhydro-1-azepinyl)ethyl]methylamino}ethyl]-2,3-dihydro-1,5(5H)-benzothiazepin-4-one oxalate A mixture of 10 g (22 mmol) of (+)-cis-(2S,3S)-3-acetyloxy-2-(4-methoxyphenyl)-5-[2-(methylamino)ethyl]2,3-dihydro-1,5(5H)-benzothiazepin-4-one in hydrochloride form, 5.2 g (29 mmol) of 1-(2-chloroacetyl)-perhydroazepine and 12.67 g (92 mmol) of potassium carbonate in 200 ml of 2-butanone is heated under reflux for 15 h.

The mixture is filtered, the filtrate is evaporated and the residue is taken up with 50 ml of chloroform and washed with 30 ml of water. The organic phase is dried over magnesium sulphate and evaporated, and the residual oil is purified by chromatography on silica gel.

The purified base is taken up with ethanol and treated with 1.46 g (16 mmol) of oxalic acid, and the precipitate is filtered off and recrystallized in ethanol.

8.21 g of oxalate are isolated.

Melting point: 147–149° C. $[\alpha]_D^{20} = +86.11°$ (c=0.5; MeOH).

EXAMPLE 5 (COMPOUND NO. 20)

(+)-cis-(2S,3S)-3-Hydroxy-2-(4-methoxyphenyl)-5-[2-{N-[2-oxo-2-(perhydro-1-azepinyl) ethyl]methylamino}ethyl]-2,3-dihydro-1,5(5H)-benzothiazepin-4-one oxalate A solution of 6.53 g (12 mmol) of (+)-cis-(2S,3S)-3-acetyloxy-2-(4-methoxyphenyl)-5-[2-{N-[2-oxo-2-(perhydro-1-azepinyl) ethyl]methylamino}ethyl]-2,3-dihydro-1,5(5H)-benzothiazepin-4-one in 100 ml of methanol is cooled to 0° C., 0.5 ml of a 6N solution of sodium methylate is added and the mixture is stirred for 4 h.

The solvent is evaporated off, and the residue is taken up with chloroform and washed successively with bicarbonate solution and then with water. The organic phase is dried and evaporated. The residual oil is taken up with 40 ml of ethanol, 0.934 g of oxalic acid is added and the product obtained is recrystallized in a 1:2 acetone/isopropyl alcohol mixture.

4.54 g of oxalate are finally isolated.

Melting point 102° C. $[\alpha_D^{20} = +82.3°$ (c =0.5; MeOH).

EXAMPLE 6 (COMPOUND NO. 37)

(+)-cis-(2S,3S)-9-Chloro-3-hydroxy-2-(4-methoxyphenyl)-5-[2-{N-[2-oxo-2-(perhydro-1-azepinyl}ethyl]methylamino}ethyl]-2,3-dihydro-1,5(5H)-benzothiazepin-4-one oxalate.

(a)

2-{N-[2-Oxo-2-(perhydro-1-azepinyl]ethyl]methylamino}ethanol

A mixture of 4.8 g (27 mmol) of 1-(2-chloroacetyl)-perhydroazepine, dissolved in 40 ml of 2-butanone, 3.6 g (48 mmol) of 2-(methylamino)ethanol and 6.6 g (48 mmol) of potassium carbonate is heated to 70° C. for 5 h.

The mixture is filtered hot, the filtrate is evaporated, the residue is taken up with dichloromethane, and the solution is washed with 1N sodium hydroxide, dried over magnesium sulphate and evaporated. 5.7 g of product are obtained, and this is used as it is in the next stage.

(b)
2-Chloro-N-methyl-N-[2-oxo-2-(perhydro-1-azepinyl)ethyl]ethylamine

A mixture of 5.7 g (27 mmol) of 2-{N-[2-oxo-2-(perhydro-1-azepinyl) ethyl]methylamino}ethanol, dissolved in 50 ml of chloroform, and 6 ml (excess) of thionyl chloride is heated under reflux for 2 h.

The mixture is then evaporated, the residue is taken up with benzene, the mixture is evaporated and the residue is taken up with ether. The solution is washed with cold 2N sodium hydroxide solution, the insoluble matter is separated by filtration, and the filtrate is dried over magnesium sulphate and evaporated.

5 g of product are obtained, and this is used as it is in the next stage.

(c)
(+)-cis-(2S,3S)-9-Chloro-3-hydroxy-2-(4-methoxyphenyl)-5-[2-{N-[2-oxo-2-(perhydro-1-azepinyl)ethyl]methylamino}ethyl]-2,3-dihydro-1,5(5H)-benzothiazepin-4-one oxalate A suspension of 4 g (12 mmol) of (+)-cis-(2S,3S)-9-chloro-2-hydroxy-2-(4-methoxyphenyl)-2,3-dihydro-1,5(5H)-benzothiazepin-4-one, 3 g (13 mmol) of 2-chloro-N-methyl-N-[2-oxo-2-(perhydro-1-azepinyl)ethyl]ethylamine and 5.5 g (39 mmol) of potassium carbonate in 60 ml of 2-butanone is heated under reflux for 18 h.

The insoluble matter is filtered off, the filtrate is evaporated, the residue is taken up with dichloromethane, and the solution is washed with bicarbonate solution, dried over magnesium sulphate and evaporated. The residue is treated with one equivalent of oxalic acid, and 5.5 g of oxalate are obtained.

Melting point: 108° C. [α] = +21° (c=1; MeOH).

EXAMPLE 7 (COMPOUND NO. 39)

(+)-cis-(2S,3S)-3-Acetyloxy-9-chloro-2-(4-methoxyphenyl)-5-[2-{N-[2-oxo-2-(perhydro-1-azepinyl)ethyl]methylamino}ethyl]-2,3-dihydro-1,5(5H)-benzothiazepin-4-one hydrochloride A mixture of 3.55 g (7 mmol) of (+)-cis-(2S,3S)-9-chloro-3-hydroxy-2-(4-methoxyphenyl)-5-[2-{N-[2-oxo-2-(perhydro-1-azepinyl) ethyl]methylamino)ethyl]-2,3-dihydroxy-1,5(5H)-benzothiazepin-4-one (free base), 30 ml of acetic acid, 30 ml of acetic anhydride and 3.5 ml of ether saturated with hydrogen chloride is heated to 100° C. for 6 h. The mixture is evaporated, the residue is taken up with toluene, the latter is evaporated off and the residue is 9round in a mixture of ethyl acetate and ether.

3.47 9 of hydrochloride are finally isolated.
Melting point: 126° C. [α] = +21.1° C. =1; MeOH).

EXAMPLE 8 COMPOUND NO. 36

(+)-cis-(2S,3S)-9-Chloro-3-hydroxy-2-(4-methoxyphenyl)-4[2-(N-[2-oxo-2-(perhydro-1-azepinyl)ethyl]methylamino}ethyl]-2,3-dihydroy-1,5(5H)-benzothiazepin-4-one oxalate The procedure is similar to that described in Example 6c), heating a mixture of 3.35 g (10 mmol) of (+)-cis-(2S,3S)-9-chloro-3-hydroxy-2-(4-methoxyphenyl)-2,3-dihydro-1,5(5H)-benzothiazepin-4-one, 2.5 g (11 mmol) of 2-chloro-N-methyl-N-[2-oxo-2-(perhydro-1-azepinyl)ethyl]ethylamine and 4.7 g (30 mmol) of potassium carbonate in 60 ml of 2-butanone to 70° C. for 20 h.

4.6 g of oxalate are finally isolated.
Melting point: 118° C.

EXAMPLE 9 (COMPOUND NO. 38)

(+)-cis-(2S,3S)-3-Acetyloxy-9-chloro-2-(4-methoxyphenyl)-5[2-{N-[2-oxo-2-(perhydro-1-azepinyl)ethyl]methylamino}ethyl]-2,3-dihydro-1,5(5H)-benzothiazepin-4-one hydrochloride The acetylation of 1.7 g of (+)-cis-(2S,3S)-9-chloro-3-hydroxy-2-(4-methoxyphenyl)-5-[2-(N-[2-oxo-2-(perhydro-1-azepinyl) ethyl]methylamino}ethyl]-2,3-dihydro-1,5(5H)-benzothiazepin-4-one oxalate under conditions similar to those of Example 7 enables 1.7 g of hydrochloride to be obtained.

Melting point: 148° C.

EXAMPLE 10 (COMPOUND NO. 33)

(+)-cis-(2S,3S)-9-Chloro-3-hydroxy-2-(4-methoxyphenyl)-5-[2-{N-[2-(1,2,3,4-tetrahydro-2-isoquinolyl)-2-oxoethyl]methylamino}ethyl]-2,3-dihydro-1,5(5H)-benzothiazepin-4-one hydrochloride (a)
2-{N-[2-oxo-2-(1,2,3,4-Tetrahydro-2-isoquinolyl)ethyl]methylamino}ethanol The procedure is similar to that described in Example 6a), reacting 4.78 g (23 mmol) of 2-(2-chloroacetyl)-1,2,3,4-tetrahydroisoquinoline and 3 g (40 mmol) of 2-(methylamino)ethanol.

5.6 g of product are obtained.

(b)
2-Chloro-N-methyl-N-[2-oxo-2-(1,2,3,4-tetrahydro-2isoquinolyl)ethyl]ethylamine.

The procedure is similar to that described in Example 6b), treating 5.6 g of 2-{N-[2-oxo-2-(1,2,3,4-tetrahydro-2-isoquinolyl) ethyl]methylamino}ethanol with an excess of thionyl chloride in chloroform.

5.2 g of product are obtained.

(c)
(+)-cis-(2S,3S)-9-Chloro-3-hydroxy-2-(4-methoxyphenyl)-5-[2-{N-[2-(1,2,3,4-tetrahydro-2-isoquinolyl)-2-oxoethyl]methylamino}ethyl]-2,3-dihydro-1,5(5H)-benzothiazepin-4-one hydrochloride The procedure is similar to tat described in Example 6c), reacting 5 g (15 mmol) of (+)-cis-(2S,3S)-9-chloro-3-hydroxy-2-(4-methoxyphenyl)-2,3-dihydro-1,5(5H)-benzothiazepin-4-one and 4.2 g (15.7 mmol) of 2-chloro-N-methyl-N-[2-oxo-2-(1,2,3,4-tetrahydro-2-isoquinolyl)ethyl]ethylamine in 2-butanone in the presence of potassium carbonate.

5.4 g of crude product are obtained, the hydrochloride of which is prepared by means of ether saturated with hydrogen chloride.

4.4 g of hydrochloride are finally obtained.
Melting point: 162° C. $[\alpha]_D^{20} = 20.3°$ (c=1; MeOH).

EXAMPLE 11 (COMPOUND NO. 35)

(+)-cis-(2S,3S)-3-Acetyloxy-9-chloro-2-(4-methoxyphenyl)-5-[2-(N-[2-(1,2,3,4-tetrahydro-2-isoquinolyl)-2-oxoethyl]methylamino}ethyl]-2,3-dihydro-1,5(5H)-benzothiazepin-4-one hydrochloride The acetylation of (+)-cis-(2S,3S)-9-chloro-3-hydroxy-2-(4-methoxyphenyl)-5-[2-(N-[2-(1,2,3,4-tetrahydro-2-isoquinolyl)-2-oxoethyl]methylamino}ethyl]-2,3-dihydro-1,5(5H)-benzothiazepin-4-one under conditions similar to those described in Example 7 enables a quantitative yield of (+)-cis-(2S,3S)-3-acetyloxy-9-chloro-2-(4-methoxyphenyl)-5-[2-{N-[2-(1,2,3,4-tetrahydro-2-isoquinolyl)-2-oxoethyl]methylamino}ethyl]-2,3-dihydro-1,5(5H)-benzothiazepin-4-one hydrochloride to be obtained.

Melting point: 146° C. $[\alpha]_D^{20} = +20./9°(c=1; MeOH)$.

The table which follows illustrates the structures and physical properties of a few compounds according to the invention.

TABLE (I)

| No | X | R1 | R2 | R3 | Salt | $[\alpha]_D^{20}$ (°) c(%), MeOH | M.p. (°C.) |
|---|---|---|---|---|---|---|---|
| 1 | H | COCH₃ | H | H | ox. | +96.6 (0.5) | 188 |
| 2 | H | COCH₃ | H | iC₃H₇ | ox. | +90 (0.5) | 119 |
| 3 | H | COCH₃ | H | iC₄H₉ | ox. | +82.8 (0.5) | 98 |
| 4 | H | COCH₃ | H | tC₄H₉ | ox. | +79.4 (0.5) | 120 |
| 5 | H | COCH₃ | H | CH₂C₆H₅ | ox. | +82.2 (0.5) | 185 |
| 6 | H | COCH₃ | CH₃ | iC₃H₇ | ox. | +79.9 (0.5) | 124 |
| 7 | H | COCH₃ | CH₃ | C₆H₅ | ox. | +79.3 (0.5) | 127 |
| 8 | H | COCH₃ | CH₃ | CH₂C₆H₅ | ox. | +73.1 (0.5) | 96 |
| 9 | H | COCH₃ | CH₃ | CH₂CH₂C₆H₅ | ox. | +75.2 (0.5) | 95 |
| 10 | H | COCH₃ | C₂H₅ | C₂H₅ | ox. | +81.8 (0.5) | 126 |
| 11 | H | COCH₃ | cC₃H₅ | C₆H₅ | ox. | +80.6 (0.5) | 107 |
| 12 | H | COCH₃ | iC₄H₉ | iC₄H₉ | mal. | +78.1 (0.5) | 112 |
| 13 | H | COCH₃ | | cyclopentyl | ox. | +81.2 (0.5) | 148 |
| 14 | H | COCH₃ | | CH(CH₃)₂-cyclopentyl | ox. | +76.7 (0.5) | 110 |
| 15 | H | COCH₃ | | cyclohexyl | ox. | +91.6 (0.5) | 145 |
| 16 | H | COCH₃ | | cyclohexenyl | ox. | +107.1 (0.5) | 152 |

TABLE-continued (I)

[Structure of compound (I): a benzothiazepine-like structure with OCH₃-substituted phenyl, S, OR1, N, C=O, connected via ethylene to N(CH₃)CH₂C(=O)N(R2)(R3), with X substituent on the fused phenyl ring]

| No | X | R1 | R2 | R3 | Salt | $[\alpha]_D^{20}$ (°) c(%), MeOH | M.p. (°C.) |
|---|---|---|---|---|---|---|---|
| 17 | H | COCH₃ | \multicolumn{2}{l|}{cyclohexyl-phenyl (R2,R3 together)} | ox. | +69.1 (0.5) | 167 |
| 18 | H | COCH₃ | \multicolumn{2}{l|}{cyclohexyl-CO-(4-F-phenyl)} | ox. | +68.5 (0.5) | 164 |
| 19 | H | COCH₃ | \multicolumn{2}{l|}{piperidinyl-(2-OCH₃-phenyl)} | diox. | +60.9 (0.5) | 128 |
| 20 | H | H | \multicolumn{2}{l|}{hexamethyleneimino (7-membered ring)} | ox. | +82.3 (0.5) | 102 |
| 21 | H | COCH₃ | \multicolumn{2}{l|}{hexamethyleneimino (7-membered ring)} | ox. | +86.11 (0.5) | 147–149 |
| 22 | H | COCH₃ | \multicolumn{2}{l|}{heptamethyleneimino (8-membered ring)} | ox. | +84.7 (0.5) | 129 |
| 23 | H | COCH₃ | \multicolumn{2}{l|}{thiazolidinyl} | ox. | +74.9 (0.5) | 145 |
| 24 | H | COCH₃ | \multicolumn{2}{l|}{thiomorpholinyl} | ox. | +88.1 (0.5) | 123 |

TABLE-continued

Structure (I):

General structure: a benzothiazepine-type ring with X-substituted phenyl fused to S, bearing a CH₂-(4-methoxyphenyl) group, CH-OR1, C(=O)-N (ring), with N-CH₂CH₂-N(CH₃)-CH₂-C(=O)-N(R2)(R3) side chain.

| No | X | R1 | R2 | R3 | Salt | $[\alpha]_D^{20}$ (°) c(%), MeOH | M.p. (°C.) |
|----|-----|-------|----|----|------|------|------|
| 25 | H | COCH₃ | (together: tetrahydropyran-linked, i.e., morpholino-type — R2,R3 form -CH₂CH₂-O-CH₂CH₂-) | | ox. | +79.9 (0.5) | 117 |
| 26 | H | COCH₃ | (together form a 1,2,3,4-tetrahydroisoquinoline: -CH₂-C₆H₄-CH₂CH₂-) | | ox. | +84.4 (0.5) | 139 |
| 27 | H | H | (together: 1,2,3,4-tetrahydroisoquinoline) | | ox. | +86.7 (0.5) | 118 |
| 28 | H | COCH₃ | (together: 1,2,3,4-tetrahydroisoquinoline) | | ox. | +77.5 (0.5) | 144 |
| 29 | H | COCH₃ | (together: 6-methoxy-1,2,3,4-tetrahydroisoquinoline) | | ox. | +73.3 (0.5) | 142 |
| 30 | H | COCH₃ | (together: 6,7-dimethoxy-1,2,3,4-tetrahydroisoquinoline) | | ox. | +68.7 (0.5) | 115 |
| 31 | H | COCH₃ | (together: 2,3,4,5-tetrahydro-1H-2-benzazepine) | | ox. | +66.9 (0.5) | 140 |
| 32 | 9-Cl | H | (together: 1,2,3,4-tetrahydroisoquinoline) | | HCl | 0 | 164 |
| 33 | 9-Cl | H | (together: 1,2,3,4-tetrahydroisoquinoline) | | HCl | +20.3 (1.0) | 162 |

TABLE-continued

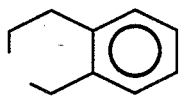

(I)

| No | X | R1 | R2 | R3 | Salt | $[\alpha]_D^{20}$ (°) c(%), MeOH | M.p. (°C.) |
|----|------|-------|----|----|------|------|------|
| 34 | 9-Cl | COCH₃ | | 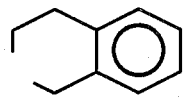 | HCl | 0 | 148 |
| 35 | 9-Cl | COCH₃ | | 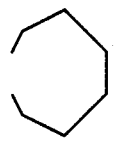 | HCl | +20.9 (1.0) | 146 |
| 36 | 9-Cl | H | |  | ox. | 0 | 118 |
| 37 | 9-Cl | H | |  | ox. | +21 (1.0) | 108 |
| 38 | 9-Cl | COCH₃ | |  | HCl | 0 | 148 |
| 39 | 9-Cl | COCH₃ | |  | HCl | +21.1 (1.0) | 126 |

Key
iC₃H₇: isopropyl
cC₃H₅: cyclopropyl
iC₄H₉: isobutyl
tC₄H₉: tert-butyl
C₆H₅: phenyl
CH₂C₆H₅: benzyl
CH₂CH₂C₆H₅: phenethyl
HCl: hydrochloride
ox.: oxalate
diox.: dioxalate
mal.: maleate The compounds of the invention were subjected to pharmacological tests to demonstrate their value as calcium antagonists.

The experimental protocol was a variant of that used by Godfraind and Kaba (1969) (Blockade or reversal of the contraction induced by calcium and adrenaline in depolarized arterial smooth muscle, Br. J. Pharmac., 36, 549–560).

The experiments were carried out on sections of rabbit thoracic aorta. The animals, "Fauves de Bourgogne" weighing 1.5 kg on average, are sacrificed by cervical dislocation and exsanguination. The thoracic aorta is rapidly removed and placed in an oxygenated Krebs bicarbonate medium (95% $O_2$+5% $CO_2$).

Sections of aorta approximately 1 cm long are prepared and installed in 20-ml organ cells containing oxygenated Krebs bicarbonate solution (pH 7.4) at 37° C. Two U-shaped metal hooks having the same length as the sections ar introduced into the bore of the latter. One of the hooks is attached to the base of the cell. The other, connected to an isometric strain gauge (Grass FTO3), permits the recording, via a continuous preamplifier (Grass 7Pl), of the contractile responses of the sections of aorta on a pen oscillograph (Grass 79B). Compared with spiral or ring-shaped preparations, this method has the advantage of having greater regard for the structural integrity of the vessels, and of recording only the radial component of the contractile responses, which represent the phenomenon of interest from the functional standpoint (regulation of arterial blood pressure). An initial tension of 4 g is applied to the preparations.

Phenoxybenzamine (1 $\mu$M) and propranolol (1 $\mu$M) are added to the different Krebs media in order to abolish the contractile responses linked to the activation of the vascular $\alpha$- and $\beta$-adrenergic receptors.

After one hour's stabilization in Krebs bicarbonate medium, the tension applied to the aorta sections is reduced to 2 g. After a delay period of 30 minutes, the preparations are incubated for about ten minutes in a Krebs bicarbonate solution without calcium in the presence of EDTA (200 $\mu$M) and propranolol (1 $\mu$M). This solution is then replaced by a depolarizing Krebs medium (rich in potassium and depleted of sodium) without calcium and containing propranolol (1 $\mu$M). After 5 minutes, a single calcium concentration of 1 mM is added to this solution, and a stabilization period of 30 minutes is observed, which enables the preparations to achieve stable contraction.

The test compounds are then added to the bath at cumulative doses, a lapse of 30 minutes (the time generally necessary for obtaining a plateau) being observed between two concentrations, until there is complete disappearance of the contraction induced by 1 mM calcium, or alternatively up to a maximum concentration of product of 30 $\mu$M. At the end of the experiment, a supramaximal concentration of papaverine (300 $\mu$M) is added in order to determine the maximum possible relaxation of each preparation The absolute values (in grams) for the initial contraction (after 1 mM $CaCl_2$) and for the contraction after the different cumulative concentrations of vasodilatory compounds are obtained, for each preparation, by difference with the minimal contraction observed 30 minutes after the final addition of 300 $\mu$M papaverine. The percentage decrease in the contraction, relative to the contraction induced by 1 mM calcium, is calculated for each concentration of compound and each preparation, and this individual percentage relaxation is averaged as X±SEM. The mean values obtained (weighted by the reciprocal of the standard error of the mean) are analysed by means of a mathematical sigmoid curve model. The molar concentration inducing 50% relaxation of the response to calcium ($EC_{50}$), or alternatively its anti-logarithm ($pEC_{50}$), is calculated.

For the compounds of the invention, the $pEC_{50}$ values are of the order of 4.5 to 7.

The compounds of the invention were also subjected to a test of inhibition of the specific binding of "PAF", platelet-activating factor.

The animals are rabbits weighing from 2.5 to 3 kg, anaesthetized with pentobarbital sodium (0.25 mg/kg intravenously) and maintained under artificial respiration by intubation. Blood is drawn from the carotid artery and collected in tubes containing a citrate-based anticoagulant. The tubes are subjected to a centrifugation at 100 g for 15 min, and the platelet-rich plasma is diluted with 2 volumes of 10 mM Tris-HCl buffer, pH 7.5, containing 150 mM sodium chloride and 2 mM EDTA (buffer A). After centrifugation at 1,000 g for 10 min at 4° C., the pellet is washed with 2 volumes of buffer A and a further centrifugation is performed.

The platelet-rich pellet is suspended in ice-cold buffer (10 mM Tris-HCl, pH 7.0, containing 5 mM magnesium chloride and 2 mM EDTA), homogenized and centrifuged at 30,000 g and at 4° C. for 10 min. This operation is repeated, the resulting pellet is collected in the same buffer and homogenized and the membrane suspension is frozen in liquid nitrogen. For the binding inhibition test, the suspension is thawed and diluted with buffer to obtain a content of approximately 150 $\mu$g of protein per milliliter.

Aliquot amounts (30 $\mu$g of protein) of membranes are incubated in the presence of 10 mM Tris-HCl buffer, pH 7.0, containing 10 mM magnesium chloride and 0.25% (weight/volume) of bovine serum albumin, for 2 h at 25° C., with 1 nM tritiated PAF ([$^3$H]-1-O-hexadecyl-2-acetyl-sn-glyceryl-3-phosphorylcholine) in a final volume of 1 ml. The incubation is stopped by collecting the membranes and washing them rapidly with ice-cold buffer on Whatman filters, using a Skatron cell collector connected to a vacuum pump. The filters are dried and assayed by scintigraphic spectrometry. The specific binding is defined by the difference in radioactivity of the membranes observed in the absence and in the presence of 1 $\mu$M tritiated PAF.

The binding inhibition tests are performed under the conditions described, in the presence of different concentrations of test compounds. The concentration $IC_{50}$ (the concentration which inhibits the specific binding by 50% is then determined for each compound by plotting the inhibition curve according to the method of least squares.

The $IC_{50}$ values of the compounds of the invention, in this test, lie between 1 and 6 $\mu$m.

Finally, the compounds of the invention were subjected to a test of inhibition of blood platelet aggregation induced by "PAF-acether" [1-O-($C_{16}$–$C_{18}$ alkyl)-2-acetyl-sn-glyceryl-3-phosphorylcholine].

The test is performed according to the method of Born [J. Physiol., (1963), 168, 178–195] on rabbit platelets. The blood is drawn by cardiac puncture and collected over 3.8% strength trisodium citrate in the proportions of 1 volume of anticoagulant solution for 9 volumes of blood. A centrifugation is then performed at 250 g for 10 min, the platelet-rich plasma is removed and the platelets are counted.

The pellet is subjected to a further centrifugation at 3,600 g for 15 min so as to obtain platelet-poor plasma, and the platelet-rich plasma is diluted by means of platelet-poor plasma to obtain a suspension containing 200,000 to 300,000 platelets per microliter.

Aggregation is induced in vitro by means of PAF-acether at the maximum concentration necessary for obtaining a maximal reversible response (normally between 1.5 and 3.3 ng/ml). The changes in optical density are recorded by means of an aggregometer (300 μl of platelet-rich plasma per cell, 1,100 rpm at 37° C.) until the point of maximal aggregation has been passed.

For the tests, the compounds of the invention are dissolved in dimethyl sulphoxide and incubated for 2 min at 37° C. before the addition of PAF-acether.

The aggregation-inhibitory action of the compounds is expressed in terms of the $IC_{50}$ concentration, the concentration which inhibits by 50% the aggregation induced by PAF-acether.

The $IC_{50}$ values of the compounds of the invention, in this test, lie between 4 and 8 μM.

The results of the tests show that the compounds of the invention are calcium antagonists, and they can, on these grounds, be used for the treatment of various conditions for which this type of agent is indicated.

Thus, in particular, they may be used in cardiovascular medicine for the treatment of conditions requiring modulators of the transmembranous and intracellular movements of calcium, most especially hypertension, angina, and cardiac arrhythmia.

They are, in addition, capable of exhibiting antiatherogenic, platelet aggregation-inhibitory, cardiac anti-ischaemic, cerebral anti-ischaemic, antimigraine, antiepileptic, antiasthmatic and antiulcer effects.

In the cardiovascular field, they may be used alone or in combination with other known active substances such as diuretics, β-blockers, angiotensin-converting enzyme inhibitors and $α_1$-receptor antagonists.

In combination with agents designed to boost their effects or decrease their toxicity, they may also be indicated for the treatment of cancer or in transplantation.

Thus the present invention also provides a compound of formula (I) or a pharmacologically acceptable acid addition salt thereof, or a pharmaceutical composition which comprises said compound or salt thereof and a pharmaceutically acceptable excipient, for use in a method of treatment of the human or animal body by therapy, especially for use in the treatment of a condition requiring a modulator of the transmembranous and intracellular movement of calcium or of a condition requiring an antiatherogenic, platelet aggregation-inhibitory, cardiac anti-ischamemic, antimigraine, antiepileptic, antiasthmatic or antiulcer agent.

The present invention further provides the use of a compound of formula (I) or a pharmacologically acceptable acid addition salt thereof in the preparation of a medicament for the treatment of a condition requiring a modulator of the transmembranous and intracellular movement of calcium or of a condition requiring an antiatherogenic, platelet aggregation-inhibitory, cardiac anti-ischaemic, cerebral anti-ischaemic, antimigraine, antiepileptic, antiasthmatic or antiulcer agent.

The compounds of the invention may be presented in all forms suitable for oral or parenteral administration, in combination with known excipients, for example in the form of tablets, hard gelatin capsules, dragees, capsules, and solutions or suspensions to be swallowed or injected.

The present invention therefore additionally provides a pharmaceutical composition which comprises a compound of formula (I) or a pharmacologically acceptable acid addition salt thereof and a pharmaceutically acceptable excipient.

The daily dosage can range, for example, from 30 to 300 mg orally and from 25 to 100 mg parenterally.

We claim:

1. A compound, in the form of a pure diastereoisomer or mixture thereof, which is a benzothiazepin-4-one derivative of formula (I):

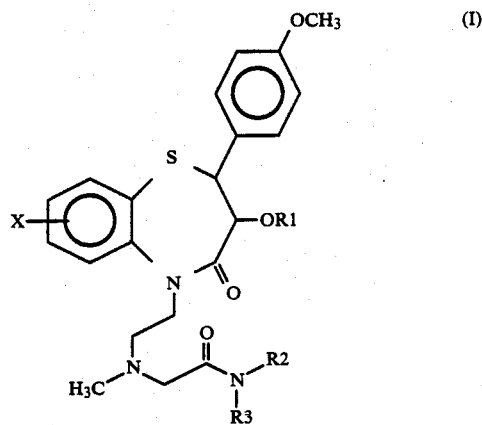

in which:
R1 is hydrogen or a $C_2$–$C_4$ alkanoyl group;
R2 and R3 independently each is hydrogen, a linear or branched $C_1$–$C_4$ alkyl group, a $C_3$–$C_5$ cycloalkyl group, a phenyl group, a benzyl group or a phenethyl group, or R2 and R3 together form, with the nitrogen atom to which they are attached, a pyrrolidinyl, 2,2-dimethylpyrrolidinyl, piperidyl, 4-phenylpiperidyl, 4-(3-methoxyphenyl)piperidyl, 4-(4-fluorobenzoyl)piperidyl, 1,2,3,6-tetrahydropyridyl, perhydroazepinyl, perhydroazocinyl, 1,3-thiazolidinyl, thiomorpholinyl, morpholinyl, 2,3-dihydroindolyl, 1,2,3,4-tetrahydroisoquinolyl, 6-methoxy-1,2,3,4-tetrahydroisoquinolyl, 6,7-dimethoxy-1,2,3,4-tetrahydroisoquinolyl or 2,3,4,5-tetrahydro-1H-benz[b]azepinyl group; and
X is hydrogen or chlorine; or a pharmacologically acceptable acid addition salt thereof.

2. A compound according to claim 1 in which R3 is a benzyl group.

3. A compound according to claim 2 which is 3-acetyloxy-2-(4-methoxyphenyl)-5-[N-{2-oxo-2-[N-(phenylmethyl)methylamino]ethyl}methylamino]ethyl}-2,3-dihydro 1,5 (5H)-benzothiazepin-4-one.

4. A compound according to claim 1 in which R2 and R3 together form, with the nitrogen atom to which they are attached, a 4-phenylpiperidyl group.

5. A compound according to claim 4 which is 3-acetyloxy-2-(4-methoxyphenyl)-5-[2-{N-[2-oxo-2-(4-phenyl-1- c piperidyl)ethyl]methylamino}ethyl]-2,3-dihydro-1,5(5H)- benzothiazepin-4-one.

6. A compound according to claim 1 in which R2 and R3 together form, with the nitrogen atom to which they are attached, a perhydroazepinyl group.

7. A compound according to claim 6 which is 3-acetyloxy-2-(4-methoxyphenyl)-5-[2-{N-[2-oxo-2-(perhydro-1-azepinyl) ethyl]methylamino}ethyl]-2,3-dihydro-1,5(5H)-benzothiazepin-4-one, 9-chloro-3-hydroxy-2(4-methoxyphenyl-5-[2-{N-[2-oxo-2-(perhydro-1-azepinyl)ethyl]methylamino}ethyl]-2,3-dihydro-1,5

(5H)-benzothiazepin-4-one or 3-acetyloxy-9-chloro-2-(4-methoxyphenyl)-5-[2{N-[2-oxo-2-(perhydro-1-azepinyl)ethyl]methylamino}ethyl-2,3-dihydro-1,5(5H)-benzothiazepin-4-one.

8. A compound according to claim 1 in which R2 and R3 together form, with the nitrogen atom to which they are attached, an unsubstituted or substituted 1,2,3,4-tetrahydroisoquinolyl group.

9. A compound according to claim 8, which is 3-acetyloxy-2-(4-methoxyphenyl)-5-[2-{N-[2-(1,2,3,4-tetrahydro-2-isoquinolyl)-2-oxoethyl]methylamino}ethyl]-2,3-dihydro-1,5(5H)-benzothiazepin-4-one, 3-acetyloxy-2(4-methoxyphenyl)-5-[2-{N-[2-(6-methoxy-1,2,3,4-tetrahydro-2-isoquinolyl)-2-oxoethyl]methylamino}ethyl]-2,3dihydro 1,5(5H)-benzothiazepin-4-one, 9-chloro-3-hydroxy-2(4-methoxyphenyl)-5-[2-{N-[2-(6-methoxy-1,2,3,4-tetrahydro-2-isoquinolyl)-2-oxoethyl]methylamino}ethyl]-2,3-dihydro-1,5(5H)-benzothiazepin-4-one or 3-acetyloxy-9-chloro-2-(4-methoxyphenyl)-5-[2-{N-[2-(1,2,3,4-tetrahydro-2-isoquinolyl)-2-oxoethyl]methylamino}ethyl]-2,3-dihydro-1,5(5H)-benzothiazepin-4-one.

10. A compound according to claim 1 which has the (+)-cis-(2S,3S) configuration.

11. A pharmaceutical composition which comprises a pharmaceutically effective amount of a compound as defined in claim 1 and a pharmaceutically acceptable excipient.

12. A method of treatment of a condition requiring a modulator of the transmembranous and intracellular movement of calcium or of a condition requiring an antiatherogenic, platelet aggregation-inhibitory, cardiac anti-ischaemic, cerebral anti-ischaemic, antimigraine, antiepileptic, antiasthmatic or antiulcer agent, which comprises adminstering to a subject in need of said treatment a compound as defined in claim 1.

* * * * *